United States Patent [19]
Dow et al.

[11] Patent Number: 5,906,988
[45] Date of Patent: *May 25, 1999

[54] METHODS OF TREATMENT USING RANOLAZINE AND RELATED PIPERAZINE DERIVATIVES

[75] Inventors: Robert James Dow, Edinburgh, United Kingdom; Pierre Ferrandon, Chilly-Mazarin, France

[73] Assignee: Syntex (U.S.A.) Inc., Palo Alto, Calif.

[ * ] Notice: This patent is subject to a terminal disclaimer.

[21] Appl. No.: 08/628,836

[22] Filed: Apr. 5, 1996

Related U.S. Application Data

[63] Continuation of application No. 07/955,397, Oct. 1, 1992, Pat. No. 5,506,229, which is a continuation of application No. 07/370,435, Jun. 23, 1989, abandoned.

[51] Int. Cl.$^6$ .................................................. A61K 31/495
[52] U.S. Cl. .............................................................. 514/255
[58] Field of Search .............................................. 514/255

[56] References Cited

U.S. PATENT DOCUMENTS 4,567,264  1/1986  Kluge et al. ............................ 514/255

OTHER PUBLICATIONS

M.C. Allely et al., "The Effects of the Novel Anti–anginal Compound RS–43285 on Myocardial Conduction in the Anaesthetized Dog", *Br. J. Pharmacol.*, 93, 375–382 (1988).
M.C. Allely et la., "The Effects of the Novel Anti–anginal Agent Ranolazine (I.D.) In a Canine Model of Transient Myocardial Ischaemia", *Br. J. Pharmacol.*, 93, 246P (1988).
P. Ferrendon et al., "Protective Effects of the Novel Anti--ischaemic Agent Ranolazine (RS–43285) in Perfused Rat Hearts", *Br. J. Pharmacol.*, 93, 247P (1988).
C.M. Brown et al., "Pharmacological Profile of Ranolazine, a Metabolic Modulator Active in Ischaemia", *Br. J. Pharmacol.*, 93, 248P (1988).
M.C. Allely et al., "The Effects of the Novel Anti–anginal Agent Ranolazine on [Lactic Acid], [K$^+$], and pH in a Canine Model of Transient Myocardial Ischaemia", *Biochem. Soc. Trans.*, 15, 1057–1058 (1987).
D. Jain et al., "Preliminary Study of a New Anti–anginal Agent (RS–43285, Syntex)", *Cardiovascular Drugs Ther.*, 1, 252 (1987).
E. Boddeke et al., "New Anti–ischaemic Drugs: Cytoprotective Action with No Primary Harmodynamic Effects", *Trends in Pharmacol. Sci.*, 10(10), 397–400 (1989).
D. Anaise et al., "The Protective Effects of Calcium Inhibitors and of Captopril on the Renal Microcirculation During Reperfusion", *Transplantation*, 43(1), 128–133 (1987).
A. Wauquier et al., "Brain Ischemia as a Target for Ca$^{2+}$ Entry Blockers", *Ann. N.Y. Acad. Sci.*, 522, 478–190 (1988).
D. Jain et al., "RS–43285 (Syntex) A Preliminary Study of a Unigue Anti–anginal Agent", *Clin. Sci.* , 73(17), 136 (1987).
*Martindale, The Extra Pharmacopoeia*, 28th ed., J.E.F. Reynolds et al., eds., The Pharmaceutical Press, London (1982), p. 636, No. 3746–e.

*Primary Examiner*—Zohreh Fay
*Attorney, Agent, or Firm*—Heller Ehrman White & McAuliffe

[57] ABSTRACT

Piperazine derivatives, particularly ranolazine, are useful for treatment of tissues experiencing a physical or chemical insult, and specifically for treating cardioplegia, hypoxic and/or reperfusion injury to cardiac or skeletal muscle or brain tissue, and for use in transplants.

17 Claims, No Drawings

METHODS OF TREATMENT USING RANOLAZINE AND RELATED PIPERAZINE DERIVATIVES

CROSS-REFERENCE TO RELATED APPLICATIONS

This application is a continuation of application Ser. No. 07/955,397, filed Oct. 1, 1992, now U.S. Pat. No. 5,506,229, which is in turn a continuation of application Ser. No. 07/370,435, filed Jun. 23, 1989, now abandoned.

BACKGROUND OF THE INVENTION

1. Field of the Invention

The present invention relates to methods of treatment using ranolazine or another piperazine derivative compound of Formula I, particularly to methods of using ranolazine for treatment of tissues experiencing a physical or chemical insult, and specifically to methods of treating cardioplegia, hypoxic and/or reperfusion injury to cardiac or skeletal muscle or brain tissue, and for use in transplants.

2. Background Information

Ranolazine, i.e., ±N-(2,6-dimethylphenyl)-4-[2-hydroxy-3-(2-methoxyphenoxy)propyl]-1-piperazine acetamide or 1-[3-(2-methoxyphenoxy)-2-hydroxypropyl]-4-[(2,6-dimethylphenyl)aminocarbonylmethyl]piperazine, and the dihydrochloride salt thereof, and the compounds of Formula I, are described in U.S. Pat. No. 4,567,264, incorporated herein by reference. Ranolazine is disclosed as a calcium entry blocking compound useful in the treatment of cardiovascular diseases, such as, myocardial infarction, congestive heart failure, angina and arrhythmia.

The anti-ischemic effects of ranolazine have been described in a number of publications, such as, Jain et al, "A PRELIMINARY STUDY OF A NEW ANTI-ANGINAL AGENT", Cardiovascular Drugs and Therapy, Vol. 1, No. 3, p. 252 (October 1987); Allely and Alps, "THE EFFECTS OF THE NOVEL ANTI-ANGINAL AGENT RANOLAZINE (I.D.) IN A CANINE MODEL OF TRANSIENT MYOCARDIAL ISCHAEMIA", Br. J. Pharmacol., 1988, 22, 246P; and by Ferrandon et al., "PROTECTIVE EFFECTS OF THE NOVEL ANTI-ISCHAEMIC AGENT RANOLAZINE (RS-43285) IN PERFUSED RAT HEARTS", Br, J. Pharmacol., 1988, 93, 247P, where utility in protecting hearts from the potentially lethal biochemical and functional injury produced: by ischaemia and/or reperfusion was reported. Tissue protection, however, is not achieved by a calcium entry blockade nor by a beta-blockade mechanism (Brown et al., Br. J. Pharmacol. 1988, 93, 248P), nor would such active agents be expected to have a tissue protective effect. Moreover, cardiodepression has been identified as a limiting factor for extensive use of CEBs in the treatment of cardio-related ischaemic conditions (Packer, et al., Circn., 75(V), 56–64, 1987; Barjon, et al., J. Am. Coll. Cardiol., 9, 622–630, 1987).

SUMMARY OF THE INVENTION

One aspect of the present invention concerns a method of treating tissues experiencing a physical or chemical insult, by administering an effective amount of a compound of Formula I:

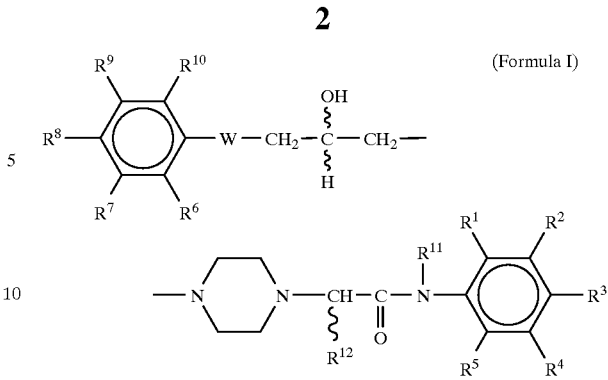

and the pharmaceutically acceptable esters and acid addition salts thereof, wherein:
$R^1$, $R^2$, $R^3$, $R^4$ and $R^5$ are each independently hydrogen, lower alkyl, lower alkoxy, cyano, trifluoromethyl, halo, lower alkylthio, lower alkyl sulfinyl, lower alkyl sulfonyl, N-optionally substituted alkylamido, except that when $R^1$ is methyl, $R^4$ is not methyl; or
$R^2$ and $R^3$ together form —OCH$_2$O—;
$R^6$, $R^7$, $R^8$, $R^9$ and $R^{10}$ are each independently hydrogen, lower acyl, aminocarbonylmethyl, cyano, lower alkyl, lower alkoxy, trifluoromethyl, halo, lower alkylthio, lower alkyl sulfinyl, lower alkyl sulfonyl, di-lower alkyl amino;
$R^6$ and $R^7$ together form —CH=CH—CH=CH—; or
$R^7$ and $R^8$ together form —OCH$_2$O—;
$R^{11}$ and $R^{12}$ are each independently hydrogen or lower alkyl; and
W is oxygen or sulfur.

In a preferred embodiment, the invention entails a method of treatment wherein the compound of Formula I is one in which $R^1$ and $R^5$ are methyl, particularly where $R^2$, $R^3$, $R^4$, $R^{11}$ and $R^{12}$ are hydrogen, and more particularly where W is oxygen. Most preferred is the method of treatment with ranolazine, i.e., where $R^6$ is methoxy and $R^7$, $R^8$, $R^9$ and $R^{10}$ are hydrogen.

In another aspect, the present invention entails a method for protecting the myocardium against global ischaemic damage induced by cardioplegia, which method comprises administering to a subject undergoing cardiac surgery, and/or adding to the extra-corporeal circulation of such subject, an effective amount of a compound of Formula I, preferably ranolazine.

The invention also entails a method for protecting skeletal muscle against damage resulting, e.g., from trauma or subsequent to muscle or systemic diseases, which method comprises administering to a subject whose skeletal muscle is or is likely to be damaged an effective amount of a compound of Formula I, preferably ranolazine.

A further aspect of this invention entails a method for treating shock conditions (including cardiogenic shock), which method comprises administering to a subject experiencing shock an effective amount of a compound of Formula I, preferably ranolazine.

Still another aspect of this invention entails a method of protecting myocardial tissue against ischaemic damage in subjects with myocardial infarction, especially in patients who are waiting to receive treatment such as thrombolytic drugs or PTCA (percutaneous transthoracic coronary angioplasty), which method comprises administering to a subject at risk of myocardial tissue ischaemic damage an effective amount of a compound of Formula I, preferably ranolazine.

Another aspect of the invention is a method for protecting neuronal tissue against ischaemia resulting from cardiac function impairment or from non-cardiac conditions (including protecting brain tissue against ischaemia-induced metabolic disorders), which method comprises administering to a subject suffering from or susceptible to suffer from neuronal tissue damage an effective amount of a compound of Formula I, preferably ranolazine.

In still another aspect, the present invention entails a method for preserving donor tissues used in transplants (protecting them from the deleterious effects of ischaemia), by administration to the donor, the recipient and/or by adding to the ex-vivo perfusion fluid an effective amount of a compound of Formula I, preferably ranolazine or a pharmaceutically acceptable salt thereof, particularly for renal transplants, skin grafts, cardiac transplants, lung transplants, corneal transplants, and liver transplants.

In yet another aspect, the invention relates to pharmaceutical compositions containing a therpeutically effective amount (up to 5 mg/ml for liquid and semi-solid formulations) of a compound of Formula I, particularly ranolazine or a pharmaceutically acceptable salt thereof, admixed with at least one pharmaceutically acceptable excipient, such compositions being adapted for use in the methods of treatment of the present invention.

Another aspect of the invention entails methods of treatment by coadministration of a compound of Formula I together with another pharmaceutically active agent, such as thrombolytic agents [especially TPA (Tissue Plasminogen Activator) or streptokinase] or anti-anginals (such as beta blockers, including propranolol and timolol).

DETAILED DESCRIPTION OF THE INVENTION

Definitions and General Parameters

The following definitions are set forth to illustrate and define the meaning and scope of the various terms used to describe the invention herein.

As used herein, the term "treatment" or "treating" means any treatment of a disease in a mammal, including:

(i) preventing the disease, that is, causing the clinical symptoms of the disease not to develop;

(ii) inhibiting the disease, that is, arresting the development of clinical symptoms; and/or (iii) relieving the disease, that is, causing the regression of clinical symptoms.

As used herein, the term "q.s." means adding a quantity sufficient to achieve a stated function, e.g., to bring a solution to the desired volume (i.e., 100%).

As used herein, the term "effective amount" means a dosage sufficient to provide treatment for the disease state being treated. This will vary depending on the patient, the disease and the-treatment being effected.

Preparation of Ranolazine

Ranolazine and the piperazine compounds of Formula I can be prepared, for example, as described in U.S. Pat. No. 4,567,264, previously incorporated herein by reference.

Utility, Testing and Administration

It has surprisingly been found that ranolazine is active in methods of treatment unrelated to its initially identified calcium entry blocking mechanism and cardioselective indications. Particularly interesting is the fact that ranolazine has now been found to protect tissues against ischaemia (improving cellular oxygen utilization efficiency) at doses that do not produce any cardiodepressant effects (see, Allely and Alps, supra. and Ferrandon, et al., supra.)

General Utility

The piperazine compounds of Formula I, particularly ranolazine and the pharmaceutically acceptable salts thereof (preferably the dihydrochloride), are useful for treating tissues experiencing a physical or chemical insult. For example, such treatment can be for cardioplegia, or for hypoxic reperfusion injury to cardiac or skeletal muscles, or brain tissue. The compounds of Formula I, particularly ranolazine and its salts, are also useful for preserving (e.g., preventing deterioration of) donor tissues used in transplants, by administration to the transplant donor, to the transplant recipient, or by perfusion of the tissues to be transplanted, particularly for renal transplants, skin grafts, cardiac transplants, lung transplants, corneal transplants, and liver transplants.

Testing

Protection of the myocardium against ischaemic damage is experimentally demonstrated by inducing infarction in a suitable test animal (e.g., a baboon) followed by examination of insult-induced elevations in enzyme levels (particularly creatine kinase "CK" and lactate dehydrogenase "LDH"). It is accepted that concentrations of these enzymes are increased after myocardial damage (Galen, et al., *J.A.M.A.*, 232, 145–147, 1975) and that such enzyme levels can be measured by an experimental test that is an adaptation of the one described by Alps, et al., (*Arzneim. Forsch Drug Res.*, 33, (1), 6, 868–876, 1983). The compounds of Formula I, as exemplified by ranolazine, are active in reducing CK and LDH enzyme levels as measured by this assay.

Protection against myocardial ischaemia can also be assessed via effectiveness to prevent ischaemia-induced increase in alpha-1 adrenoceptor number in the myocardium. It is known that alpha-1 adrenoceptor population increases in the myocardium suffering from ischaemia (Heathers, et al., *Circulation Research*, 61, 735–746, 1987). It has also been shown that alpha-1 adrenoceptor antagonists have beneficial effects during ischaemia in animal models (Wilbur, et al., *J. Cardiovascular Pharmacol.*, 10, 96–106, 1987). Thus agents which prevent the ischaemia-induced increase in alpha-1 adrenoceptors density are beneficial during myocardial ischaemia. The ability of compounds of Formula 1, as exemplified by ranolazine, to inhibit the ischaemia-induced increase of alpha-1 adrenoceptors in myocardium is assessed in the rat left ventricle using a model of ischaemia described by Allely and Brown (*Br. J. Pharmacol.*, 95, 705P, 1988). A detailed description is set forth in Example 6.

Protection of skeletal muscles against damage resulting, for example, from major surgical practices, was experimentally assessed in the same model used to assess its protective effects at the myocardial level. For this purpose skeletal muscle-specific isoenzymes $CK_3$ and $LDH_5$, are assayed as indications of damaged muscle (Galen, *Med. Times*, 105(2), 89–99, 1977). A detailed description is set forth in Example 2.

Protection of the myocardium against deleterious effects of ischaemia induced by open-heart and other cardiac surgical procedures, including cardioplegia, is assessed by a method modified from Langendorff, which entails measuring coronary effluent pH and lactate level. These tracers are recognised as indicative of tissue damage induced by severe reduction in the nutrient supply to the heart (Armiger, et al., *Biochem. Med.*, 29, 265–267, 1983; van Gilst, et al., *Archives of Pharmacol.*, suppl., 33, 161P, 1985). A detailed description is set forth in Example 3.

The utility of compounds of Formula I, as exemplified by ranolazine, in organ transplant is demonstrated by administering the test compound to pigs before nephrectomy, and/or by adding the compound to the fluid used for flushing and storage of the organ and by assessing functionality of transplanted kidneys over a period of 14 days. Improvement of renal function in treated animals is assessed by measurement of the glomerular filtration rate and also by peak serum levels for creatinine and urea. Glomerular filtration is a well established indicator of renal function (see, e.g., Mudge and Weiner in *The Pharmacological Basis of Therapeutics,* Goodman and Gilman, 879, 7th Ed, 1985) and it is generally assessed by measurement of inulin and/or creatinine clearance (*Textbook of Medicine,* 1088–93, 14th Ed., 1975— Beeson and McDermott Editors). A detailed description is set forth in Example 4.

Cerebral ischaemia is the result of either a generalized or a localized prolonged reduction of blood flow to the brain. Such a blood flow reduction can result from various pathological conditions including cerebral venous inflammation and thrombosis, cardiac diseases, changes in blood (clotting, viscosity, anaemia) or from cardiac surgical practices. One of the indications of damage produced by cerebral ischaemia is the increase of the iso-enzyme creatinephosphokinase 1 ($CPK_1$) in the plasma (Rossi, et al., *Am. J. Cardiol.,* 58(13), 1236–1241, 1986). Inhibition of the peripheral appearance of $CPK_1$ is an indication of reduced damage caused by ischaemia to the brain. This is demonstrated by administration of a test compound prior to coronary artery ligation in the baboon, as a bolus i.v. injection followed by an infusion over the period of reperfusion, as described by Alps, et al., (*Arzneim. Forsch Drug Res.,* 33, (1), 6, 868–876, 1983).

Administration

Administration of ranolazine in pure form or in an appropriate pharmaceutical composition can be carried out via any of the accepted modes of administration of agents for serving similar utilities. Thus, administration can be, for example, orally, nasally, parenterally or topically, including by perfusion. Administration can be achieved in the form of solid, semi-solid, lyophilized powder, or liquid dosage forms, such as for example, tablets, suppositories, capsules, powders, solutions, suspensions, emulsions, creams, lotions, aerosols, ointments or the like, preferably in unit dosage forms suitable for simple administration of precise dosages. The compositions will include a conventional pharmaceutical carrier or excipient and an effective amount of ranolazine or a pharmaceutically acceptable salt thereof, and in addition, may include other medicinal agents, pharmaceutical agents, carriers, adjuvants, etc. Sustained release and slow release formulations for maintaining extended or constant dosage levels are also useful in the present invention. Ranolazine can also be co-administered other active agents, such as thrombolytic agents [especially TPA (Tissue Plasminogen Activator) or streptokinase] or anti-anginals (such as beta blockers, including propranolol and timolol).

The preferred method of administration is parenteral, except for those cases when the subject must be pre-treated before surgery or when the subject must be maintained under therapy after acute episodes of ischaemia (in which instances it may be preferable to administer the composition orally).

Generally, depending on the intended mode of administration, the pharmaceutically acceptable compositions will contain about 1% to about 99% by weight of the pharmaceutically active compound of this invention and 99% to 1% by weight of suitable pharmaceutical excipients.

Preferably, the composition will be about 5 to 75% by weight of a pharmaceutically active compound, with the rest being suitable pharmaceutical excipients. For liquid and semi-solid formulations, about 5 mg/ml is preferred as the maximum concentration for the active ingredient.

Oral administration entails using a convenient daily dosage regimen which can be adjusted according to the degree of affliction. For such oral administration, a pharmaceutically acceptable, non-toxic composition is formed by the incorporation of any of the normally employed excipients, such as, for example, pharmaceutical grades of mannitol, lactose, starch, magnesium stearate, sodium saccharine, talcum, cellulose, glucose, gelatin, sucrose, magnesium carbonate, and the like. Such compositions take the form of solutions, suspensions, tablets, capsules, powders, sustained release or slow release formulations and the like.

Preferably the oral compositions will take the form of a capsule or tablet and thus the composition will contain, along with the active ingredient, a diluent such as lactose, sucrose, dicalcium phosphate, and the like; a disintegrant such as starch or derivatives thereof; a lubricant such as magnesium stearate and the like; and a binder such as a starch, gum acacia, polyvinylpyrrolidone, gelatin, cellulose and derivatives thereof, and the like.

The active compounds may be formulated into a suppository using, for example, about 0.5% to about 50% active ingredient disposed in a carrier of polyethylene glycols (PEG) [e.g., PEG 1000 (96%) and PEG 4000 (4%)] or semi-synthetic glycerides (Witepsol, suppocire).

Another preferred mode of administration is parenterally. Liquid pharmaceutically administerable compositions can, for example, be prepared by dissolving, dispersing, etc. an active compound (about 0.5% to about 20%), as described above, and Optional pharmaceutical adjuvants in a carrier, such as, for example, water, saline, aqueous dextrose, glycerol, ethanol and the like, to thereby form a solution or suspension.

For preservation of tissues awaiting, transplantation, a perfusion solution is preferred. Such solutions include an active compound in a carrier such as Eurocollins Solution (Fresenius, A. G., Bad Homburg, vdH, Germany), University of Wisconsin Fluid (Kalayoglu, M., et al., *The Lancet,* 1988 i, 617), phosphate buffered sucrose (see, e.g., Example 7E) and Hyperosmolar Citrate (Ross, et al., *Transplantation,* 1976, 498–501).

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

Actual methods of preparing such dosage forms are known, or will be apparent, to those skilled in this art; for example, see *Remington's Pharmaceutical Sciences,* 16th Ed., (Mack Publishing Company, Easton, Pa., 1980). The composition to be administered will, in any event, contain a quantity of the active compound(s) in a pharmaceutically effective amount for relief of the particular condition being treated when administered in accordance with the teachings of this invention.

Example 7 describes oral and parenteral formulations containing ranolazine. Such formulations should not be construed as narrowing the invention. In particular, parenteral formulations can be given as dilutions with perfusion fluids, dyalisis fluids and/or fluids used to flush and store organs. It is also intended that the invention encompasses the possibility to associate ranolazine with other pharmaceutical agents, as co-prescription or by concomitant dissolution in fluids.

Dosage

Generally, ranolazine is administered in a therapeutically effective amount, i.e., a dosage sufficient to effect treatment. The amount of active compound administered will, of course, be dependent on the subject treated, the subject's weight, the severity of the affliction, the route of administration and the judgement of the prescribing physician. However, absent sufficient time to weigh the foregoing factors in detail, e.g., in emergency situations, effective i.v. dosages range from about 0.05 to about 5 mg/kg for bolus injection followed by an infusion ranging from about 0.3 to about 30 mg/kg/hour. Preferably, the i.v. bolus dosage ranges from about 0.1 to about 2.5 mg/kg and the infusion dosage from about 1.5 to about 15 mg/kg/hour. For an average 70 kg human, the i.v. bolus would range from about 3.5 to about 350 mg, or preferably, from about 15 to about 105 mg. In other situations, the oral dosage is in the range of about 35 to about 1400 mg per day, preferably about 70 to about 700 mg/day, for an average 70 kg human. For administration by perfusion fluid, a concentration of about 0.001 to about 5 g per liter is used, preferably about 0.005 to about 2.5 g per liter, and most preferably about 0.005 to about 0.1 g per liter; perfusion can continue from tissue removal from the donor until its use for transplantation.

EXAMPLES

The following preparations and examples are given to enable those skilled in the art to more clearly understand and to practice the present invention. They should not be considered as limiting the scope of the invention, but merely as being illustrative and representative thereof.

EXAMPLE 1

Protection Against Cardiac Ischaemia

This is an adaptation of the test described by Alps, et al., (*Arzneim. Forsch Drug Res.*, 33, (1), 6, 868–876, 1983).

Eight male baboons were anaesthetized then randomly allocated to one of the two following groups:

Group A (control group)

Four animals were subjected to 30 min. occlusion of the left anterior descending- coronary artery (LAD) followed by a reperfusion period of 5.5 hours. Venous plasma samples taken pre-thoracotomy, pre-LAD ligation and every hour during the reperfusion period were analyzed for $CPK_2$ and $LDH_1$ iso-enzyme levels.

Group B (treated group)

As in group A, except that the animals received a loading dose of ranolazine (500 ug/kg) intravenously 10 min. before LAD ligation followed by a continuous infusion of 50 ug/kg/min. for a 6-hour period starting at LAD ligation time.

RESULTS $CPK_2$ iso-enzyme levels in plasma remained below the detection limits until the first hour post-infarction. $LDH_1$ plasma levels were identical at pre-surgery and pre-ligation times (pre-infarct period). Results, as reported in Table 1, are expressed in international units of iso-enzyme per liter of plasma.

TABLE 1

| Group | Time | Pre-Pre-infarct | 1 hr Post-reperfusion | 6 hr Post-reperfusion |
|---|---|---|---|---|
| Control group | $CPK_2$ | N.D. | 10.5 | 232.8 |
| | $LDH_1$ | 52.7 | — | 333.8 |
| Tested group | $CPK_2$ | N.D. | 11.0 | 28.5 |
| | $LDH_1$ | 53.0 | — | 85.8 |

As shown above, ranolazine strongly inhibited the release of $CPK_2$ and $LDH_1$, such a result being indicative of an effective protection of the myocardial tissue against deleterious effects of ischaemia.

EXAMPLE 2

Skeletal Muscle Protection

Skeletal muscle protection was determined according to the experimental conditions as per Example 1, except that plasma samples were assayed-for $CPK_3$ and $LDH_5$ iso-enzymes. The results are reported in Table 2.

TABLE 2

| Group | Time | Pre-surgery | Post-reperfusion 6 hr Post-infarct |
|---|---|---|---|
| Control group | $CPK_3$ | 104.6 | 2016.5 |
| | $LDH_5$ | 30.0 | 212.0 |
| Tested group | $CPK_3$ | 84.0 | 141.0 |
| | $LDH_5$ | 27.4 | 22.3 |

Iso-enzyme levels are given in International Units per liter of plasma.

Thus, ranolazine clearly protected the muscle from surgery-induced damage.

EXAMPLE 3

Myocardial Protection During Cardioplegia

This method has been described by Ferrandon et al., *Br. J. Pharmacol.*, 93, 247P, 1988.

Male Sprague-Dawley rats were anaesthetized with pentobarbitone sodium (50 mg/kg, i.p.). After injection of heparin (200 units i.v.) the thorax was opened, the heart removed with a length of aorta attached and then immersed in ice cold Krebs' solution (118 mM NaCl, 4.55 mM KCl, 1.2 mM $KH_2SO_4$, 1.2 mM $MgSO_4$, 11.0 mM glucose, 20.0 mM $NaHCO_3$, 1.35 mM $CaCl_2$, pH 7.4). The heart was gently palpated to expel the blood. Hearts were then perfused with the above solution warmed to 37° C. and gassed with 95% $O_2$ and 5% $CO_2$ retrogradely via the aorta (Langendorff model) using a peristaltic pump set to deliver 14 ml/min. A microelectrode was introduced into the ventricular muscle wall and a reference electrode placed in contact with the perfusion fluid 3 cm above the heart. The two electrodes were connected to a pH meter.

Hearts were perfused at 14 ml/min for a 15 min period to obtain a stable baseline ventricular pH. The aortic flow was then reduced to 1 ml/min for 15 min by decreasing the pump speed. The flow was then restored to the initial rate for 15 min. Values of coronary flow and ventricular pH were measured at 5 minute intervals. After restoration of the initial flow rate measurements were made at 30 seconds, 1 minute and 5 min. Samples of coronary effluent were collected and stored on ice. Infusions of ranolazine (1 μM) were started 10 min prior to reducing the flow rate and were continued for the remainder of the experiment. At the end of the experiment the atria were removed and the hearts dried at 75° C. for 2 days.

Biochemical determination of lactate released into the coronary effluent was made using a spectrophotometric method. The quantity of lactate contained in the samples was obtained by reference to a standard curve. Lactate release from the heart mass was calculated using the following formula:

$$\frac{[\text{lactate}] \, (\text{microMol}/ml) \times \text{coronary flow} \, (ml/\text{min})}{\text{dry weight of the heart} \, (g)}$$

The results are reported in Tables 3 and 4.

TABLE 3

| | pH Modifications | | |
|---|---|---|---|
| | Pre-ischeamia | After 10 min of low perfusion | Fall in pH |
| CONTROLS | 7.36 | 6.77 | 0.59 |
| RANOLAZINE | 7.38 | 7.10 | 0.28 |

Thus, ranolazine inhibits the ischaemia-induced fall in pH by aproximately 50%.

TABLE 4

Lactate release modifications*

| Group | 2 min before low perf. | 5 min after low perf. | 15 min after low perf. | 1 min after reperf. |
|---|---|---|---|---|
| CONTROLS | 0.6 | 3.34 | 5.0 | 17.4 |
| 1 $\mu$M RANOLAZINE | 1.2 | 2.45 | 2.5 | 8.0 |

*Values are expressed as micromoles of lactate released per minute in the coronary effluent by 1 g of dried heart.

Thus, the compounds belonging to this invention clearly reduced the sequelae of low flow perfusion.

EXAMPLE 4

Protection For Organ Transplants

Twenty left nephrectomised pigs were autotransplanted with their kidneys after preservation for 24 hours in phosphate buffered sucrose (PBS 140) and immediate contralateral nephrectomy followed the autotransplantation.

The quality of the preservation and post-transplant renal function were assessed by measurement of glomerular filtration rate (GFR) using inulin clearance on day 7.

Group A (n=10) placebo group

The animals received placebo pre-treatment (bolus and infusion) commencing 5 min prior to left nephrectomy and lasting until the kidney was removed. The kidney was then flushed with PBS 140 containing placebo before storage in PBS 140. After 24 hours storage the kidney was auto-transplanted.

Group B (n=10) treated group

The animals received a bolus dose of ranolazine intravenously (0.85 mg/kg) 5 min prior to nephrectomy followed by an infusion (0.25 mg/kg/h) until the kidney was removed. The kidney was then flushed with PBS 140 solution containing ranolazine 0.5 mg/l (made up immediately before flush) prior to storage. After 24 hours storage the kidney was auto-transplanted.

TABLE 5

| | Group A | | Group B | |
|---|---|---|---|---|
| Glomerular filtration rate at day 7 | 16.4 | ml/min | 56.6 | ml/min |
| Peak Serum Urea | 43.4 | mM/l | 28.5 | mM/l |
| Peak Serum Creatinine | 1063 | $\mu$M/l | 750 | $\mu$M/l |

The results shown in Table 5 demonstrate that organs preserved in a fluid containing ranolazine achieved superior functionality after transplantation as compared with the control group that did not receive ranolazine.

EXAMPLE 5

Protection Against Brain Ischaemia

Isoenzyme appearance in peripheral venous blood was determined according to the experimental conditions as per Example 1, except that plasma samples were assayed for $CPK_1$. The results are reported in Table 6.

TABLE 6

| | $CPK_1$ Levels | |
|---|---|---|
| | Pre-surgery | 6 hr post-infarct |
| CONTROL GROUP | 18.8 | 85.7 |
| RANOLAZINE GROUP | 19.9 | 19.3 |

Results are expressed in International Units per liter of plasma, and clearly demonstrate the protective role of ranolazine in cerebral ischaemia.

EXAMPLE 6

Protection Against Myocardial Ischaemia

Male Sprague-Dawley rats were pentobarbitone-anaethetized and mechanically respired with room air. A left lateral thoracotomy was then performed and the left anterior descending coronary artery (LAD) was occluded for a period of 30 min. Control animals had the ligature placed in position but not tied.

Compounds (500 ug/kg ranolazine, saline vehicle) were administered either i.p. or i.v. 15 min prior to LAD ligation or i.p. for 3 days (twice a day) plus 15 min prior to occlusion.

At the end of the ischaemic period the ischaemic zone of the left ventricle was excised and analyzed for alpha-1-adrenoceptor density according to the method described by Williams et al. (*Cardiovascular Pharmacology*, 3, 522, 1981). The apparent alpha-1-adrenoceptor density was calculated at 0.1 nM [$^3$H]-prazosin and results were expressed as femtomole of receptors per mg of protein, as shown in Table 7. These results demonstrate that ranolazine inhibits the ischaemia-induced increase in $\alpha$-1 adrenoreceptor density in rats left ventricle and is therefore useful to prevent tissue damage resulting from myocardial ischaemia.

TABLE 7

| Group | Route | No. Animals | Alpha-1 density |
|---|---|---|---|
| Control | | 12 | 8.65 |
| Ischaemia/Treated by saline vehicle only | | 12 | 16.30 |

TABLE 7-continued

| Group | Route | No. Animals | Alpha-1 density |
|---|---|---|---|
| Ischaemia/Treated by ranolazine | i.p. | 13 | 11.20 |
| Ischaemia/Treated by ranolazine | i.v. | 9 | 9.71 |
| Ischaemia/Treated by ranolazine | i.p. 3 days | 9 | 8.33 |

EXAMPLE 7

Formulations

The following example illustrates the preparation of representative pharmaceutical formulations containing a compound of Formula I, as exemplified by ranolazine.

| A. I.V. FORMULATION (low concentration) | | | | |
|---|---|---|---|---|
| (ranolazine) | 5.0 | mg | 0.5 | g |
| dextrose monohydrate | 51.2 | mg | 5.1 | g |
| sodium hydroxide q.s. to | pH 4 | | pH 4 | |
| water for injection to | 1.0 | ml | 100 | ml |
| B. I.V. FORMULATION (high concentration) | | | | |
| (ranolazine) | 200.0 | mg | 2 | g |
| dextrose monohydrate | 39.4 | mg | 4 | g |
| sodium hydroxide q.s. to | pH 4 | | pH 4 | |
| water for injection to | 1.0 | ml | 100 | ml |

To prepare the I.V. formulations, ranolazine and dextrose monohydrate are dissolved into water (70 per cent of the final desired volume) then sodium hydroxide (10 N solution) is added under stirring until pH 4 and the volume is completed to 100 ml with water. The medium is filtered through a 0.2 micron membrane filter and packaged in ampoules or vials under sterile conditions. Alternatively the medium can be filtered under non-sterile conditions, packed in ampoules then sterilized by autoclaving.

| C. FILM COATED TABLET FORMULATION | |
|---|---|
| Ingredients | Parts by weight |
| ranolazine HCl (A) | 80.0 |
| microcrystalline cellulose (B) | 16.5 |
| polyvinylpyrrolidone (C) | 1.0 |
| crosscarmellose sodium (D) | 2.0 |
| magnesium stearate (E) | 0.5 |

(A), (B) and half of (D) are mixed then (C) and water are added to allow wet granulation. (E) and the remaining part of (D) are finally added. After careful mix the granulated mixture is dried, formed into tablets containing up to 250 mg of active compound, and the tablets are film coated using White Opadry following appropriate techniques.

| D. CONTROLLED RELEASE FORMULATION | |
|---|---|
| Ingredients | Parts by weight |
| ranolazine BASE (A) | 90 |
| microcrystalline cellulose (B) | 10 |

The two above ingredients are dry mixed then water is added to form a wet mass adequate for extrusion then spheronisation (0.5 to 1.4 mm). Microspheres are coated with appropriate release-controlling polymers then put into hard shell capsules containing up to 250 mg of active ingredient per unit.

| E. PERFUSION FLUID | |
|---|---|
| Ingredients | Parts by weight |
| Ranolazine | 20 mg |
| Phosphate Buffered Sucrose | |
| Sucrose | 48.0 g |
| Sodium Dihydrogen Phosphate | 4.59 g |
| Sodium Monohydrogen Phosphate | 6.53 g |
| Water For Injection (U.S.P.) | q.s. to 1000 ml |

The ingredients are dissolved in a portion of the Water For Injection, and once dissolved, the remaining volume is made up with Water For Injection.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of protecting tissues against ischaemic damage selected from:
   (a) protecting the myocardium against global ischaemic damage induced by cardioplegia, and
   (b) protecting neuronal tissue against ischaemic damage resulting from cardiac function impairment or from non-cardiac conditions, the method comprising administering a therapeutically effective amount of a compound of the formula:

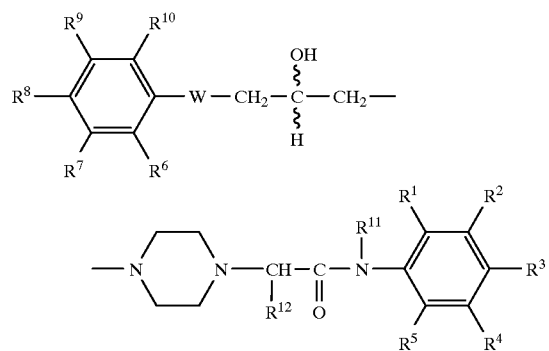

or a pharmaceutically acceptable ester or acid addition salt thereof, where:

$R^1$, $R^2$, $R^3$, $R^4$ and $R^5$ are each independently hydrogen, lower alkyl, lower alkoxy, cyano, trifluoromethyl, halo, lower alkylthio, lower alkyl sulfinyl, lower alkyl sulfonyl, or N-optionally substituted alkylamido (except that when $R^1$ is methyl, $R^4$ is not methyl); or $R^2$ and $R^3$ taken together form —$OCH_2O$—;

$R^6$, $R^7$, $R^8$, $R^9$ and $R^{10}$ are each independently hydrogen, lower acyl, aminocarbonylmethyl, cyano, lower alkyl, lower alkoxy, trifluoromethyl, halo, lower alkylthio, lower alkyl sulfinyl, lower alkyl sulfonyl, di(lower alkyl) amino; or $R^6$ and $R^7$ together form —CH=CH—CH=CH—; or $R^7$ and $R^8$ together form —OCH$_2$O—;

$R^{11}$ and $R^{12}$ are each independently hydrogen or lower alkyl; and

W is oxygen or sulfur.

2. A method of protecting the myocardium against global ischaemic damage induced by cardioplegia, the method comprising administering a therapeutically effective amount of a compound of the formula:

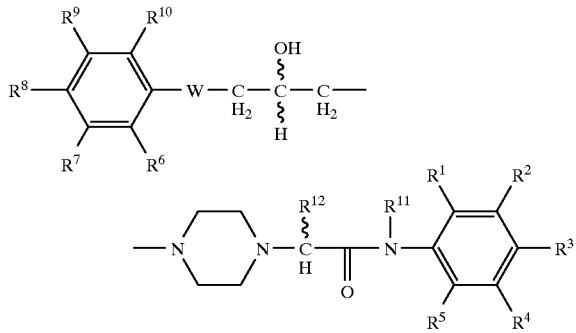

or a pharmaceutically acceptable ester or acid addition salt thereof, where:

$R^1$, $R^2$, $R^3$, $R^4$ and $R^5$ are each independently hydrogen, lower alkyl, lower alkoxy, cyano, trifluoromethyl, halo, lower alkylthio, lower alkyl sulfinyl, lower alkyl sulfonyl, or N-optionally substituted alkylamido (except that when $R^1$ is methyl, $R^4$ is not methyl); or $R^2$ and $R^3$ taken together form —OCHO$_2$—;

$R^6$, $R^7$, $R^8$, $R^9$ and $R^{10}$ are each independently hydrogen, lower acyl, aminocarbonylmethyl, cyano, lower alkyl, lower alkoxy, trifluoromethyl, halo, lower alkylthio, lower alkyl sulfinyl, lower alkyl sulfonyl, di(lower alkyl) amino; or $R^6$ and $R^7$ together form —CH=CH—CH=CH—; or $R^7$ and $R^8$ together form —OCH$_2$O—;

$R^{11}$ and $R^{12}$ are each independently hydrogen or lower alkyl; and

W is oxygen or sulfur.

3. The method of claim 2 where $R^1$ and $R^5$ are methyl.

4. The method of claim 3 where $R^2$, $R^3$, $R^4$, $R^{11}$ and $R^{12}$ are hydrogen.

5. The method of claim 4 where W is oxygen.

6. The method of claim 5 where the compound is ranolazine or a pharmaceutically acceptable salt thereof.

7. The method of claim 6 where the compound is a pharmaceutically acceptable salt of ranolazine.

8. The method of claim 7 where the compound is ranolazine dihydrochloride.

9. The method of claim 2 comprising systemically administering the compound to a subject undergoing cardiac surgery.

10. The method of claim 9 comprising adding the compound to the extra-corporeal circulation of a subject undergoing cardiac surgery.

11. A method of protecting neuronal tissue against ischaemic damage resulting from cardiac function impairment or from non-cardiac conditions, the method comprising administering a therapeutically effective amount of a compound of the formula:

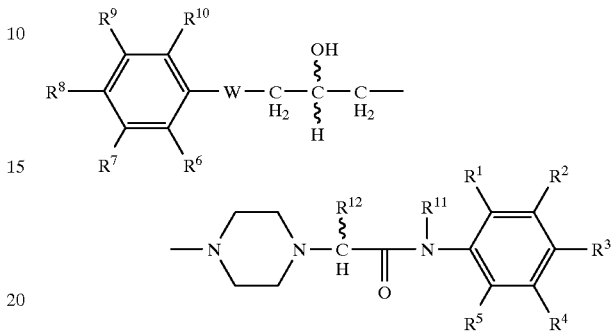

or a pharmaceutically acceptable ester or acid addition salt thereof, where:

$R^1$, $R^2$, $R^3$, $R^4$ and $R^5$ are each independently hydrogen, lower alkyl, lower alkoxy, cyano, trifluoromethyl, halo, lower alkylthio, lower alkyl sulfinyl, lower alkyl sulfonyl, or N-optionally substituted alkylamido (except that when $R^1$ is methyl, $R^4$ is not methyl); or $R^2$ and $R^3$ taken together form —OCH$_2$O—;

$R^6$, $R^7$, $R^8$, $R^9$ and $R^{10}$ are each independently hydrogen, lower acyl, aminocarbonylmethyl, cyano, lower alkyl, lower alkoxy, trifluoromethyl, halo, lower alkylthio, lower alkyl sulfinyl, lower alkyl sulfonyl, di(lower alkyl) amino; or $R^6$ and $R^7$ together form —CH=CH—CH=CH—; or $R^7$ and $R^8$ together form —OCH$_2$O—;

$R^{11}$ and $R^{12}$ are each independently hydrogen or lower alkyl; and

W is oxygen or sulfur.

12. The method of claim 11 where $R^1$ and $R^5$ are methyl.

13. The method of claim 12 where $R^2$, $R^3$, $R^4$, $R^{11}$ and $R^{12}$ are hydrogen.

14. The method of claim 13 where W is oxygen.

15. The method of claim 14 where the compound is ranolazine or a pharmaceutically acceptable salt thereof.

16. The method of claim 15 where the compound is a pharmaceutically acceptable salt of ranolazine.

17. The method of claim 16 where the compound is ranolazine dihydrochloride.

* * * * *